United States Patent
Guha et al.

(10) Patent No.: US 10,054,722 B2
(45) Date of Patent: Aug. 21, 2018

(54) SUB THZ TO MID INFRARED TUNABLE SEMICONDUCTOR PLASMONICS

(71) Applicants: IHP GmbH—Innovations for High Performance Microelectronics/Leibniz-Institut fur Innovative Mikroelektronik, Frankfurt (Oder) (DE); Universitat Kassel, Kassel (DE)

(72) Inventors: Subhajit Guha, Frankfurt (DE); Thomas Schroder, Berlin (DE); Bernd Witzigmann, Kassel (DE); Giovanni Capellini, Berlin (DE)

(73) Assignee: IHP GMBH—INNOVATIONS FOR HIGH PERFORMANCE MICROELECTRONICS/LEIBNIZ-INSTITUT FUR INNOVATIVE MIKROELEKTRONIC, Frankfurt (Oder) (DE)

( * ) Notice: Subject to any disclaimer, the term of this patent is extended or adjusted under 35 U.S.C. 154(b) by 2 days.

(21) Appl. No.: 15/460,604

(22) Filed: Mar. 16, 2017

(65) Prior Publication Data
US 2017/0269267 A1     Sep. 21, 2017

(30) Foreign Application Priority Data

Mar. 18, 2016  (EP) ..................................... 16161267
Apr. 25, 2016  (DE) ........................ 10 2016 206 999

(51) Int. Cl.
*G02B 5/00*     (2006.01)
*G01N 21/55*    (2014.01)
(Continued)

(52) U.S. Cl.
CPC .............. *G02B 5/008* (2013.01); *G01N 21/35* (2013.01); *G01N 21/553* (2013.01); *G02F 1/015* (2013.01); *G02F 2203/10* (2013.01)

(58) Field of Classification Search
CPC ....... G01N 21/35; G01N 21/553; G02B 5/008; G02F 1/015; G02F 2203/10
See application file for complete search history.

(56) References Cited

U.S. PATENT DOCUMENTS

| 2005/0270538 A1 | 12/2005 | Meehan et al. |
| 2010/0316078 A1 | 12/2010 | Ono |

(Continued)

FOREIGN PATENT DOCUMENTS

| KR | 20070094727 A | 9/2007 |

OTHER PUBLICATIONS

Yao, et al; "Broad electrical tuning of graphene-loaded optical antennas"; The Optical Society; Jun. 9, 2013; pp. 1-2.

*Primary Examiner* — Mark R Gaworecki
(74) *Attorney, Agent, or Firm* — Ware, Fressola, Maguire & Barber LLP (57) ABSTRACT

A tunable plasmon resonator, comprising a plasmon resonance layer made of graphene, a crystalline group-IV-semiconductor material or a crystalline group-III-V semiconductor material, and arranged on a carrier substrate, the plasmon resonance layer having a plasmon resonance region that is exposed to a sensing volume and a tuning device that is integrated into the plasmon resonator and arranged and configured to modify a density of free charge carriers in the plasmon resonance region or to modify an effective mass amount of the free charge carriers in the plasmon resonance region by applying of a control voltage to tuning control electrode(s) of the tuning device, thereby setting a plasmon frequency of plasmon polaritons in the plasmon resonance region to a desired plasmon frequency value within a (Continued)

plasmon frequency tuning interval, for resonance excitation of plasmon polaritons by incident electromagnetic waves of a frequency corresponding to the set plasmon frequency value.

15 Claims, 6 Drawing Sheets

(51) Int. Cl.
*G01N 21/35* (2014.01)
*G02F 1/01* (2006.01)
*G01N 21/552* (2014.01)
*G02F 1/015* (2006.01)

(56) References Cited

U.S. PATENT DOCUMENTS

| | | |
|---|---|---|
| 2011/0032528 A1 | 2/2011 | Charette |
| 2012/0074323 A1 | 3/2012 | Gomez rivas et al. |
| 2014/0224989 A1 | 8/2014 | Long et al. |
| 2015/0369735 A1 | 12/2015 | Avouris et al. |

SUB THZ TO MID INFRARED TUNABLE SEMICONDUCTOR PLASMONICS

CROSS REFERENCE TO RELATED APPLICATION

This application claims priority under 35 USC § 119 to European Patent Application No. 16 161 267.6 filed on Mar. 18, 2016 and German Patent Application No. 10 2016 206 999.3 filed on Apr. 25, 2016. Both applications are hereby incorporated by reference in their entirety.

TECHNICAL FIELD

The present invention relates to a tunable plasmon resonator, a sensor device, to a sensor arrangement, and to a method for fabricating a tunable plasmon resonator.

BACKGROUND OF THE INVENTION

In metals, free electrons with an equilibrium electron density exhibit collective longitudinal density oscillations referred to as plasmons having an eigenfrequency called the plasmon frequency. The presence of a boundary formed by a surface gives rise to a further mode of oscillation, namely surface waves forming surface plasmons. Surface plasmons thus are collective oscillations of free electrons at the surface.

Surface plasmons at an interface of a metal with a dielectric can couple with a propagating electromagnetic field (photons) giving rise to surface-plasmon polaritons. These surface-plasmon polaritons propagate along the surface. Thus, interaction of light with electromagnetic waves in metal structures gives rise to electromagnetic fields arising from surface plasmon polaritons. The strength of the electromagnetic field associated with a surface-plasmon polariton decreases exponentially with increasing distance from the surface, both inside and outside the metal. Since surface plasmon polaritons propagate along the boundary of the metal and an external dielectric medium, they are sensitive to any change of the boundary, such as the adsorption of molecules on the conducting surface.

Metal plasmonic structures have been explored for application in waveguides, sensors, and modulators. Due to enhanced field strength, which is a typical property of surface plasmon polaritons, surface-plasmon-based biosensors for sensing of biomolecules promise an extremely high sensitivity, which is suitable for detection of even a single biomolecule arranged in proximity to the surface. Therefore, surface-plasmon-based biosensors seem ideally suited for lab-on-chip applications.

Due to the plasmon frequencies in metals, the operating frequency of known metal plasmonic structures is in the visible spectral range. The decay length governing the decrease of the field strength of the electromagnetic field of the surface plasmon polaritons in a dielectric fluid volume above the metal surface (herein called the sensing volume) is of the order of nanometers, thus, aiding in near field sensing of biomolecules up to the order of nanometers.

In order to be able to identify and distinguish between different biomolecules, spectroscopic measurements are often necessary, requiring an availability of surface-plasmon polaritons covering a frequency spectrum of interest. Tuning the plasmon frequency of the plasmons, however, is extremely difficult in known metallic structures. Hence, establishing a spectroscopy platform using plasmonic structures remains an open task.

SUMMARY OF THE INVENTION

According to a first aspect of the present invention, a tunable plasmon resonator is provided comprising:
- a plasmon resonance layer made of graphene, a crystalline group-IV-semiconductor material or a crystalline group-III-V semiconductor material, and arranged on a carrier substrate, the plasmon resonance layer having a plasmon resonance region that is exposed to a sensing volume. This is the plasmon resonator whose resonance frequency is dependent on the geometry of the resonator. The plasmon frequency defines the refractive index contrast.
- a tuning device that is integrated into the plasmon resonator and arranged and configured
  - to modify the density of free charge carriers in the plasmon resonance region of the resonance layer or to modify the effective mass of the free charge carriers in the plasmon resonance region of the resonance layer by application of a control voltage to one or more tuning control electrodes of the tuning device, and
  - to thus set a plasmon frequency of plasmon polaritons in the plasmon resonance region to a desired plasmon frequency value within a plasmon frequency tuning interval, for resonance excitation of plasmon polaritons by incident electromagnetic waves of a frequency corresponding to the set plasmon frequency value.

The tunable plasmon resonator of the first aspect of the present invention is based on a semiconductor structure having free charge carriers in a plasmon resonance layer. The plasmon resonator is not based on exciting surface plasmons as in metals, but on a larger volume of plasma resonance in the plasmon resonance layer. As is known per se, the plasmon frequency in a semiconductor is dependent on the concentration of free charge carriers within the semiconductor and on the effective mass of the charge carriers. This is expressed in the Drude-Lorentz relation $$\omega_p^2 = \frac{Nq^2}{\varepsilon_0 m}$$

wherein $\omega_p$ is the plasmon frequency, N is a charge carrier density, q is the elementary charge, $\varepsilon_0$ is the vacuum permittivity constant, and m the effective mass of the free charge carriers. The concentration of free charge carriers can be influenced by doping during fabrication on one hand, but on the other hand also by injection of free charge carriers under operation of the tunable plasmon resonator, which means under application of a suitable tuning control voltage via the tuning device. Furthermore, the effective mass of the free charge carriers can be influenced by material selection during fabrication on one hand, but on the other hand also by subjecting the lattice of the semiconductor plasmon resonance layer to mechanical stress, which may be a compressive or tensile stress. Application of stress influences the effective mass of the free charge carriers in the semiconductor plasmon resonance layer. Therefore, both mentioned measures, influencing the density of free charge carriers and influencing the effective mass of the free charge carriers in the plasmon resonance layer, can be used to tune the plasmon frequency in the plasmon resonance layer. The measures can be applied in combination or in the alternative.

Due to the typical free charge carrier densities and effective masses in semiconductor materials, the tunable semiconductor plasmon resonator is suitable for operation in the sub-terahertz to mid infrared spectral range of the electromagnetic spectrum. The suggested tunable semiconductor plasmon resonator thus forms a key to obtaining information about absorption and vibrational properties of large molecules such as biomolecules, which information can be obtained exactly in the sub-terahertz to mid infrared spectral range.

An advantage of the semiconductor plasmon resonator of the present invention is that it also allows a tuning of the resonator's quality factor. Due to the larger field penetration in semiconductor materials, this is achieved only in semiconductor plasmonics and not in metal plasmonics. This makes the volume of the semiconductor significant which plays the role of tuning the quality factor of the device. In metals, this being a surface phenomenon, volume of the device plays no role in it and hence such a quality factor tuning is not possible.

Furthermore, embodiments of the tunable plasmon resonator of the invention can be based on materials and structures that are compatible with standard semiconductor fabrication processes, such as CMOS or BiCMOS. This reduces the cost of manufacturing, especially for lab-on-chip designs containing a large number of semiconductor plasmon resonator structures according to the present invention.

In the following, embodiments of the tunable plasmon resonator will be explained.

There are different possibilities of tuning the plasmon frequency that can be used in the alternative or in combination with each other.

One possibility is actively controlling and thus tuning the concentration of free charge carriers in the plasmon resonance layer. In one embodiment, which implements this possibility the plasmon resonance layer is a semiconductor layer of intrinsic conductivity, the tuning device comprises a first tuning layer formed by a first doped semiconductor layer of a first conductivity type and a second tuning layer formed by a second doped semiconductor layer of a second conductivity type opposite to the first conductivity type, each of the first and second tuning layers being connected with a respective first or second tuning control electrode, and wherein the plasmon resonance layer is arranged between the first and second tuning layers to form a p-i-n structure, thus allowing an injection of free charge carriers into the plasmon resonance layer in a density amount that depends on an injection control voltage applied via the first and second tuning control electrodes.

in another embodiment that makes use of the possibility of tuning the charge carrier density provided by the tunable plasmon resonator of the present invention, the plasmon resonance layer is a semiconductor layer of a first conductivity type, the tuning device comprises a tuning layer formed by a doped semiconductor layer of a second conductivity type opposite to the first conductivity type, each of the plasmon resonance layer and the tuning layer being connected with a respective first or second tuning control electrode, and wherein the plasmon resonance layer and the tuning layer are arranged to form a p-n junction, the plasmon resonance region lying a depletion region under application of a maximum reverse bias voltage and containing injected free charge carriers in a density amount that depends on an injection control voltage applied via the first and second tuning control electrodes. The injection control voltage is to be provided in forward direction in one variant. In another variant, an injection control voltage applied in backward direction is to be used, for instance with a voltage amount generating hot-carrier or avalanche carrier injection.

In yet another embodiment that makes use of the tunability of the charge carrier density, the plasmon resonance layer is a semiconductor layer of a first conductivity type, the tuning device comprises a tuning layer formed by metal layer each of the plasmon resonance layer and the tuning layer being connected with a respective first or second tuning control electrode, and wherein the plasmon resonance layer and the tuning layer are arranged to form a Schottky junction, the plasmon resonance region lying a depletion region under application of a maximum reverse bias voltage and containing injected free charge carriers in a density amount that depends on an injection control voltage applied in forward direction via the first and second tuning control electrodes.

Further embodiments make use of the possibility of the tunable plasmon resonator of the present invention of tuning the effective mass of the free charge carriers in the plasmon resonance layer.

In one of these embodiments, the tuning device comprises a piezoelectric stressor layer configured and arranged to be deformed piezoelectrically and to thus exert stress on a crystal lattice of the plasmon resonance layer with a stress amount depending on a strain control voltage applied to the piezoelectric stressor via at least one strain control electrode, thus modifying a lattice strain amount present in the plasmon resonance layer and in turn changing an effective mass of the free charge carriers in the plasmon resonance layer. Preferably, the stressor layer is arranged between the carrier substrate and the plasmon resonance layer.

In another embodiment that makes use of varying effective masses of the free charge carriers for varying the plasmon frequency, the plasmon resonance layer has different material compositions in different lateral sections. The different material compositions are associated with different effective mass amounts of the free charge carriers in the respective lateral section. In this embodiment, the different lateral sections give rise to resonance at different plasmon frequencies. The resonance layer as a whole can therefore respond to different incoming frequencies.

In one embodiment that makes use of a combination of the mentioned different possibilities of tuning the plasmon frequency the plasmon resonance layer is a semiconductor layer of intrinsic conductivity, the tuning device comprises a first tuning layer formed by a first doped semiconductor layer of a first conductivity type and a second tuning layer formed by a second doped semiconductor layer of a second conductivity type opposite to the first conductivity type, each of the first and second tuning layers being connected with a respective one of a first and second tuning control electrode, the plasmon resonance layer is arranged between the first and second tuning layers, thus allowing an injection of free charge carriers into the plasmon resonance layer in a density amount that depends on an injection control voltage applied via the first and second tuning control electrodes, and wherein the tuning device further comprises a piezoelectric third tuning layer configured and arranged to be deformed piezoelectrically and to thus exert tensile stress on the plasmon resonance layer with a stress amount depending on a strain control voltage applied to the tuning layer via at least one strain control electrode, thus modifying a lattice strain amount present in the plasmon resonance layer and in turn changing an effective mass of the free charge carriers in the plasmon resonance layer.

The structure of the tunable plasmon resonator preferably has the plasmon resonance layer comprising two layer segments. Front faces of the two layer segments face each other and form field enhancement regions. The sensing volume is formed by a gap between the front faces. The field enhancement is achieved by providing the two front faces as open facets. In one advantageous variant of this embodiment, the two layer segments, when seen in a top view, each have the shape of a wedge and together are arranged to form a bow—tie—shaped configuration. In a preferred implementation of this variant, the tip wedge segment length corresponds to half a resonance wavelength, a tip facet width is about a tenth of the wavelength, and a distance of the tip facets from each other is about a fraction of the wavelength.

For a given geometry of the resonator, the resonance frequency is varied by the properties of the charge carriers (carrier density and the effective mass). This is also true for the case where for a given charge carrier property the geometry of the resonator defines the resonance frequency and can be subsequently tuned by altering the geometry of the resonator.

In embodiments of the present invention, the plasmon resonator is a geometric resonator that allows altering the carrier properties to obtain tunability of the resonance frequency. The resonance frequency of the given resonator can be varied by altering the density of free charge carriers (suitably electrons), wherein the achievable frequency range can be influenced by doping during fabrication of the plasmon resonator. Another way to alter the resonance frequency is changing the effective mass of the free charge carriers. This can be influenced by varying lattice stress in the plasmon resonator.

In one embodiment, the carrier substrate has an opening that exposes a bottom surface section of the plasmon resonance layer on a second substrate side opposite to a first substrate side comprising the plasmon resonance region.

The carrier substrate is preferably made of silicon. Suitably silicon (100) is used as the carrier substrate. Other semiconductor materials can be used for the carrier substrate, depending on the active material used in the resonance layer.

According to a second aspect of the present invention a sensor device is provided. The sensor device comprises at least one tunable plasmon resonator according to an embodiment of the first aspect to of the invention. The sensor device further comprises a sensor chamber enclosing a sensing volume to be filled with a dielectric fluid under test for a detection of particles in the dielectric fluid under test. The dielectric fluid can be a liquid or gaseous dielectric medium.

In order to prove the performance of the sensor device, a preferred embodiment comprises a plurality of pointed nanostructures extending from a bottom of the sensor chamber into the sensing volume.

According to a third aspect of the present invention, a sensor arrangement is provided. The sensor arrangement comprises
    a sensor device according to the second aspect of the invention or one of its embodiments,
    a tunable emitter arranged and configured to provide electromagnetic radiation in a sub-terahertz to mid-infrared frequency range incident on the exposed plasmon resonance region of the sensor device; and
    a detector arranged and configured to detect electromagnetic radiation in the THz to infrared frequency range provided by the emitter and either reflected or transmitted by the plasmon resonance region of the sensor device The sensor arrangement of the third aspect of the invention shares the advantages of the previous aspects of the invention. It is suitable for use in the sub-terahertz to mid infrared spectral range of the electromagnetic spectrum and preferably used in the terahertz frequency range.

The term sub-terahertz is used to denote frequencies in the range between 0.3 and less than 1 THz. The mid infrared frequency region covers frequencies of up to 100 THz, whereas in some embodiments a maximum frequency is at about 40 THz.

A fourth aspect of the present invention is formed by a method for fabricating a tunable surface—plasmon resonator for operation at frequency in an infrared frequency range. The method comprises
    fabricating a plasmon resonance layer made of a crystalline semiconductor material on a carrier substrate,
    exposing a plasmon resonance region of the plasmon resonance layer to a sensing volume to be filled with a dielectric fluid;
    fabricating an integrated tuning device that is arranged and configured
        to modify a density of free charge carriers in the plasmon resonance region of the resonance layer or to modify an effective mass amount of the free charge carriers in the plasmon resonance region of the resonance layer by application of a control voltage to one or more tuning control electrodes of the tuning device, and
        to thus set a plasmon frequency of plasmon polaritons in the plasmon resonance region to a desired plasmon frequency value within a plasmon frequency tuning interval, for resonance excitation of plasmon polaritons by incident electromagnetic waves of a frequency corresponding to the set plasmon frequency value.

BRIEF DESCRIPTION OF THE DRAWINGS

In the following, further embodiments will be described with reference to the attached drawings. In the drawings.

DETAILED DESCRIPTION

Figure 1:
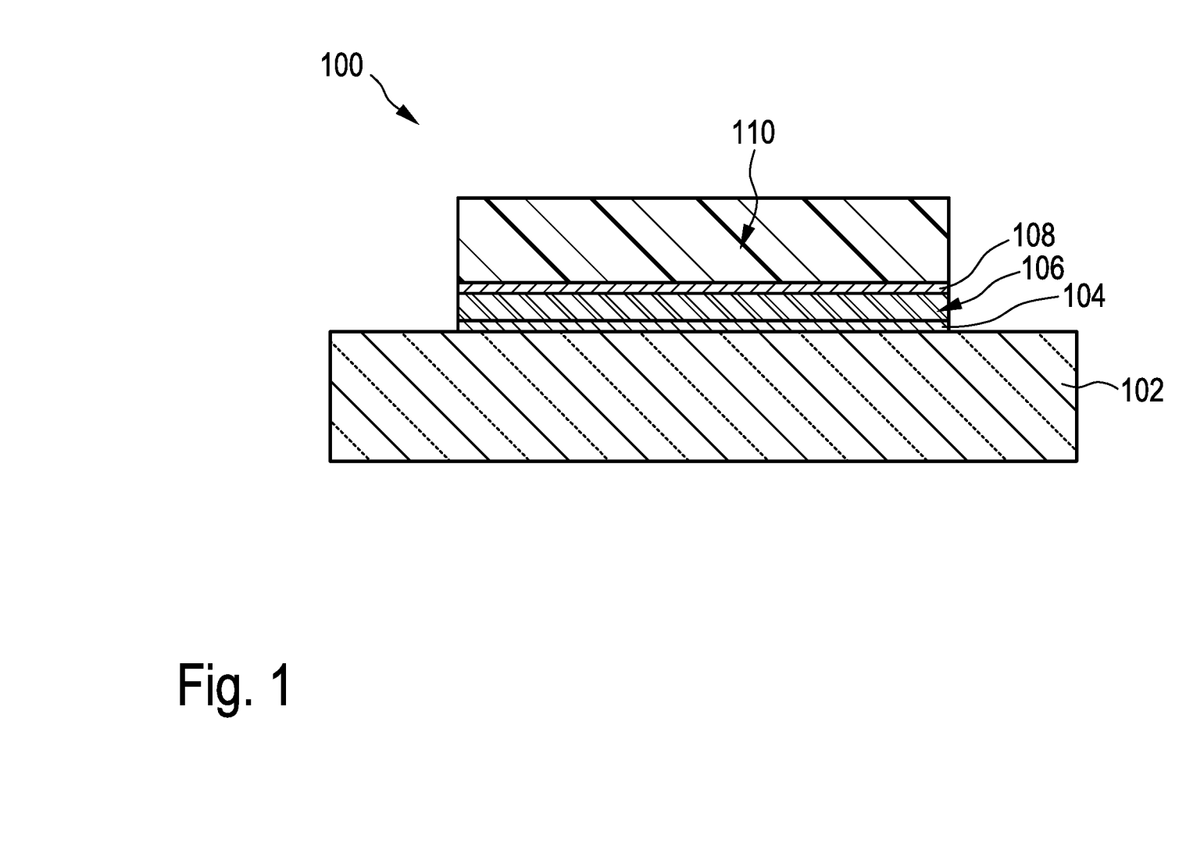
FIG. 1 is a schematic cross sectional view of a first embodiment of tunable semiconductor plasmon resonator structure.

FIG. 1 is a schematic cross sectional view of an embodiment of a tunable semiconductor plasmon resonator structure 100. The illustration of the plasmon resonator structure 100 is schematic and simplified in that only the layers that are of importance for explaining the general device structure are shown.

The plasmon resonator structure 100 comprises a bottom layer 102, which forms a carrier substrate. The bottom layer 102 may for instance be made of silicon, suitably silicon (100), or silicon dioxide. A first contact layer 104 is arranged on the bottom layer 102, followed in a stacking direction by a piezoelectric stressor layer 106, and a second contact layer 108. The first and second contact layers 104 and 108 are made of a metal. They are connectable with an external tuning control device (not shown), from which they can receive a strain control voltage.

On the second contact layer 108, a plasmon resonance layer 110 is arranged. The plasmon resonance layer is made of a semiconductor material. Suitable semiconductor materials for the plasmon resonance layer are group-IV semiconductors such as silicon, germanium, or a silicon germanium alloy, a III-V semiconductor material, or graphene. The semiconductor material of the plasmon resonance layer 110 is doped and has a certain volume density N of free charge carriers. This carrier density N is suitably in a range between $1 \times 10^{17}$ cm$^{-3}$ and $5 \times 10^{20}$ cm$^{-3}$.

While generally the free charge carriers can be either electrons or holes, the present non-limiting example makes use of free electrons. The plasmon resonance layer 110 is in direct contact with the underlying stack comprising the piezoelectric stressor layer 106 embedded between the contact layers 104 and 108.

The layer stack of the piezoelectric stressor layer 106 embedded between the contact layers 104 and 108 forms an integrated tuning device that is configured and arranged to exert stress on the crystal lattice of the plasmon resonance layer 110 with a stress amount depending on the strain control voltage applied to the piezoelectric stressor layer 106 via the contact layers 104 and 108. By piezoelectric deformation of the piezoelectric stressor layer 106, a lattice strain amount present in the plasmon resonance layer 110 is induced, in turn an effective mass of the free charge carriers in the plasmon resonance layer 110 is changed. The change of the effective mass of the free charge carriers—determines the plasmon frequency of the plasma of free charge carriers in the plasmon resonance layer according to the Drude-Lorentz relation given above.

In operation of the semiconductor plasmon resonator 100, therefore, the piezoelectric stressor layer 106 is used as a tuning layer to tune the resonance frequency of the resonator to a desired value by tuning the effective mass of the carriers. Plasmon polaritons in the plasmon resonance layer 110 can be excited by impinging electromagnetic radiation of a corresponding frequency provided by an external source of radiation. The resonance excitation of the plasmon polaritons allows exposing a sensing volume adjacent to the plasmon resonance layer and filled with a dielectric fluid containing particles under test to an enhanced field strength, which is a typical property of plasmon polaritons. Particles under test showing a characteristic frequency response within a spectral tuning interval of the plasmon resonance frequency can thus be detected and identified with high sensitivity. This high sensitivity is of particular advantage in the field of bio sensing applications, where it reaches the sensitivity level of detecting even a single biomolecule.

Figure 2:
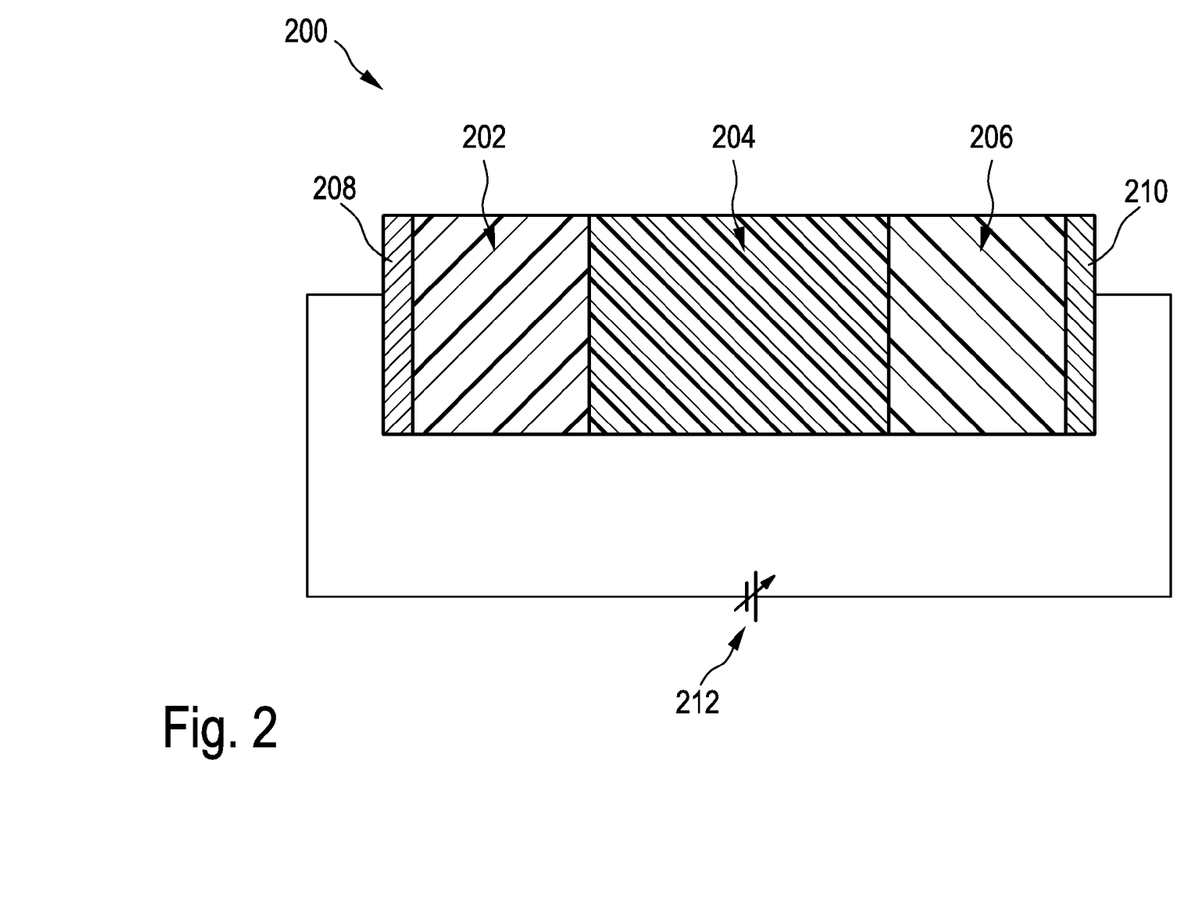
FIG. 2 is a schematic illustration of a second embodiment of a tunable semiconductor plasmon resonator structure.

FIG. 2 is a schematic illustration of a second embodiment of a tunable semiconductor plasmon resonator structure 200. The tunable semiconductor plasmon resonator structure 200 of FIG. 2 forms a lateral p-i-n junction with a p-doped semiconductor layer 202, an intrinsic semiconductor layer 204 and an n-doped semiconductor layer 206. In this embodiment, the plasmon resonance layer is formed by the semiconductor layer 204 of intrinsic conductivity, and the integrated tuning device is formed by the p-doped semiconductor layer 202 as a first tuning layer and the n-doped semiconductor layer 206 as a second tuning layer. The tuning layers are connected with respective first and second tuning control electrodes 208 and 210. Thus, the intrinsic semiconductor layer 204 that forms the plasmon resonance layer is laterally embedded between the first and second tuning layers to form a p-i-n structure. This allows controlling concentration of free charge carriers in the intrinsic semiconductor layer 204 in a charge-carrier density amount that depends on a control voltage provided by a tunable voltage source 212 via the first and second tuning control electrodes 208 and 210.

The control voltage is in one variant of this embodiment applied in reverse bias. This allows controlling the density of free charge carriers in the intrinsic semiconductor layer 204 by increasing or decreasing depletion width, wherein the initial (V=0) doping concentration amounts of the p-doped semiconductor layer 202 and of the n-doped semiconductor layer 206 provide for the maximum density of free charge carriers in the intrinsic semiconductor layer 204, and thus the maximum of the tunable plasmon frequency range.

In another variant of this embodiment, the control voltage is applied in forward bias. This allows increasing the density of free charge carriers in the intrinsic semiconductor layer 204 with increasing amount of the control voltage.

In both variants, the controllable variation of the charge-carrier density amount in the intrinsic semiconductor layer 204 that forms the plasmon resonance layer corresponds with a controllable variation of the plasmon resonance frequency.

Figure 3:
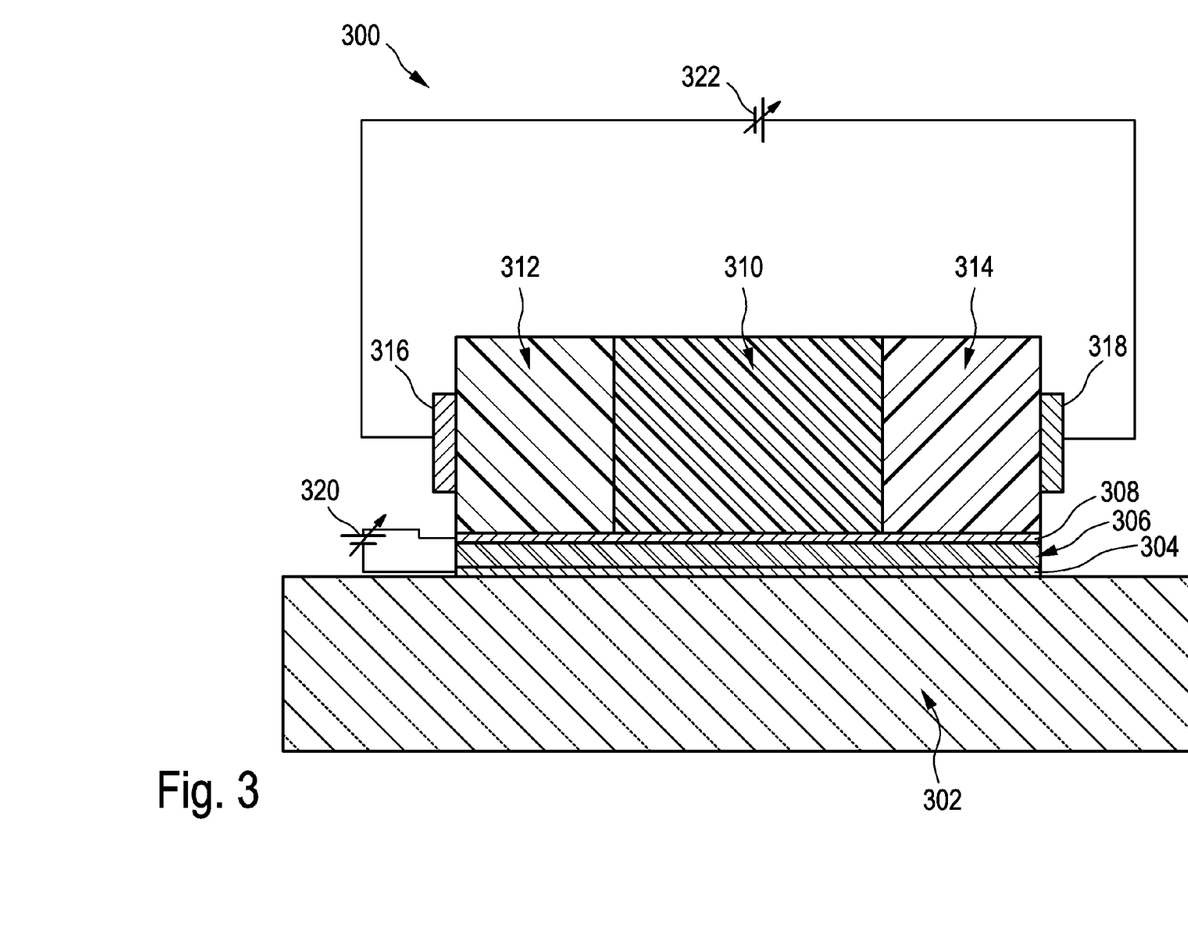
FIG. 3 is a schematic cross sectional view of a third embodiment of a tunable semiconductor plasmon resonator structure.

FIG. 3 is a schematic cross sectional view of a third embodiment of a tunable semiconductor plasmon resonator structure 300.

As with FIGS. 1 and 2, the illustration of the plasmon resonator structure 300 is schematic and simplified in that only the layers that are of importance for explaining the general device structure are shown.

The plasmon resonator structure 300 is essentially a combination of the embodiments of FIGS. 1 and 2. It comprises a bottom layer 302, a first contact layer 304, a piezoelectric stressor layer 306, and a second contact layer 308. The first and second contact layers 104 and 108 are connectable with an external tuning control device 320, from which they can receive a strain control voltage.

On the second contact layer 308, a plasmon resonance layer 310 is arranged. The plasmon resonance layer 310 is made of an intrinsic semiconductor material. The plasmon resonance layer 310 is in direct contact with the underlying stack comprising the piezoelectric stressor layer 306 embedded between the contact layers 304 and 308.

The plasmon resonance layer 310 forms a part of a lateral p-i-n junction with a p-doped semiconductor layer 312, the intrinsic semiconductor layer forming the plasmon resonance layer 310 and an n-doped semiconductor layer 314.

The p-doped semiconductor layer 312 thus forms a first tuning layer and the n-doped semiconductor layer 314 forms a second tuning layer. The tuning layers are connected with respective first and second tuning control electrodes 316 and 318. Thus, the intrinsic semiconductor layer that forms the plasmon resonance 310 layer is laterally embedded between the first and second tuning layers to form a p-i-n structure.

The semiconductor plasmon resonator 300 thus allows two forms of control of the plasmon frequency, which may be applied individually or in combination with each other to achieve a desired plasmon frequency. The layer stack of the piezoelectric stressor layer 306 embedded between the contact layers 304 and 308 forms a first integrated tuning device that is configured and arranged to exert stress on the crystal lattice of the plasmon resonance layer 310 with a stress amount depending on the strain control voltage applied to the piezoelectric stressor layer 306 via the contact layers 304 and 308. By piezoelectric deformation of the piezoelectric stressor layer 306, a lattice strain amount present in the plasmon resonance layer 310 is modified, in turn an effective mass of the free charge carriers in the plasmon resonance layer 110 is changed. The change of the effective mass of the free charge carriers influences the plasmon frequency of the plasma of free charge carriers in the plasmon resonance layer according to the Drude-Lorentz relation given above. A second integrated tuning device is formed by the p-doped semiconductor layer 312 and the n-doped semiconductor layer 314. This allows controlling concentration of free charge carriers in the intrinsic semiconductor layer forming the plasmon resonance layer 310 in a charge-carrier density amount that depends on a control voltage provided by a tunable voltage source 322 via the first and second tuning control electrodes 316 and 318. The charge carrier concentration and the effective mass can thus be tuned in a way such that they shift the plasmon frequency in the same direction. This may involve changing the polarity of the voltage bias for the piezo-electric stressor.

Figure 4:
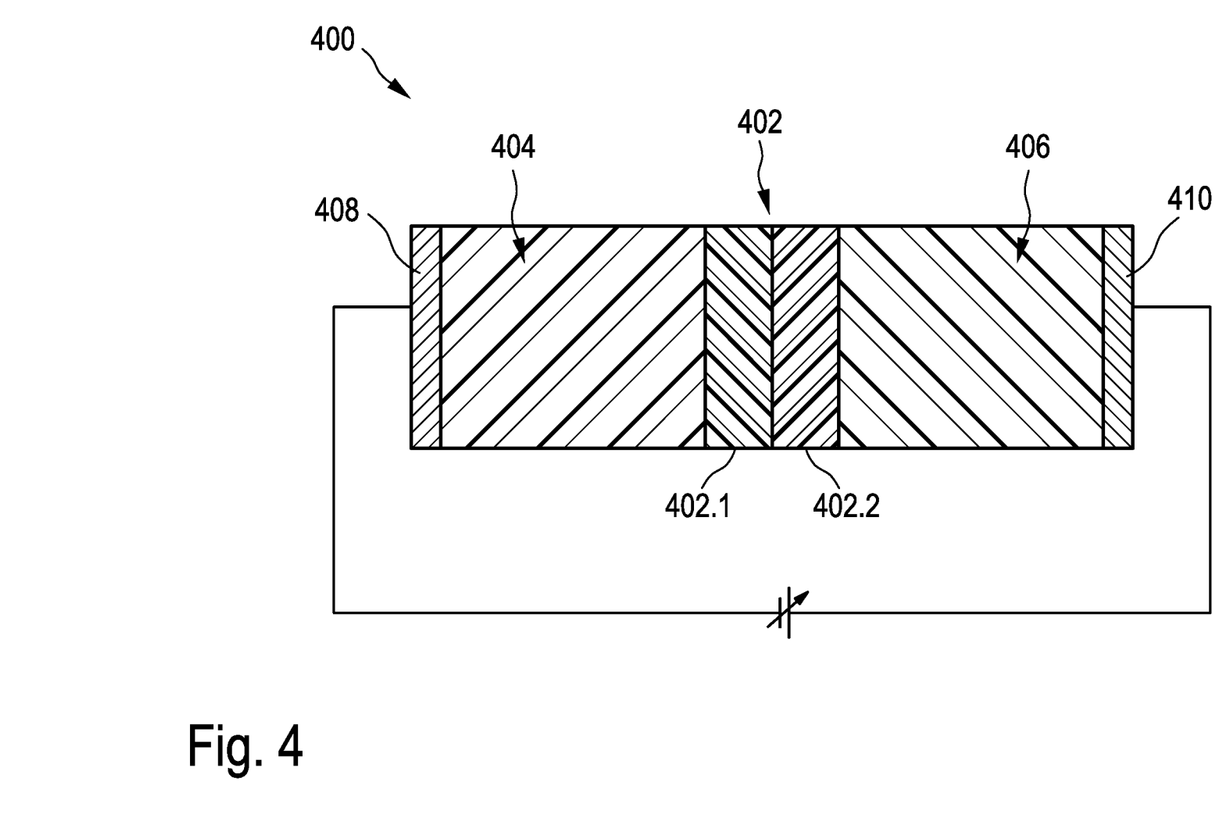
FIG. 4 is a schematic cross sectional view of a fourth embodiment of a tunable semiconductor plasmon resonator structure.

FIG. 4 is a schematic cross sectional view of a fourth embodiment of a tunable semiconductor plasmon resonator structure 400. A plasmon resonance layer 402 is embedded laterally in a lateral p-n junction with a p-doped semiconductor layer 404, and an n-doped semiconductor layer 406. The plasmon resonance layer 402 is made of two different semiconductor layers 402.1 and 402.2 which differ in their material and thus effective mass.

The present example shows the plasmon resonance layer with two different layers. However, any number of layers can be used to achieve a desired variety of materials in the plasmon resonance layer and thus a desired range of effective masses. Varying the stoichiometry of binary, ternary or quaternary alloys of III-V semiconductors, or of group IV semiconductors render orders of magnitude variation in the effective mass, which may additionally be influenced by suitable doping during fabrication.

The p-doped semiconductor layer 404 forms a first tuning layer and the n-doped semiconductor layer 406 forms a second tuning layer. The tuning layers are connected with respective first and second tuning control electrodes 408 and 410.

One way of tuning the plasmon frequency is selecting a desired sub-layer 402.1 or 402.2 for THz interaction, by operating the PN junction in depletion mode with a suitable bias voltage in reverse bias condition of the PN junction and of an amount achieving depletion of the non-selected layer while maintaining a desired concentration of free charge carriers in the selected layer. The bias voltage thus controls a position and width of the depletion region and in turn the cross section of the plasmonic area as seen by the electromagnetic radiation.

Figure 5:
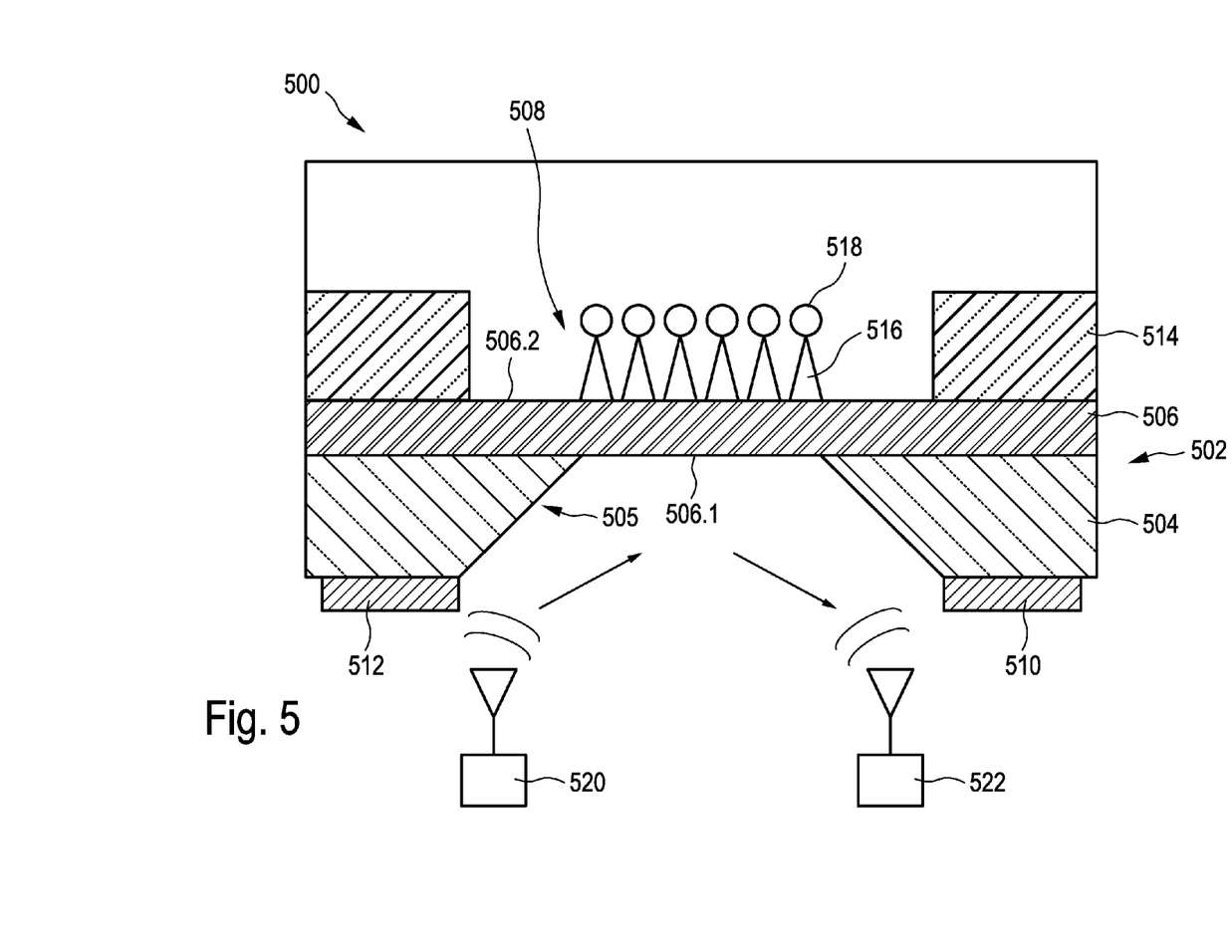
FIG. 5 is a schematic cross sectional view of a sensor device based on a tunable semiconductor plasmon resonator structure.

FIG. 5 is a schematic cross sectional view of a sensor device 500 based on a tunable semiconductor plasmon resonator structure. FIG. 5 is also a schematic representation of an embodiment of a sensor arrangement.

The sensor device 500 comprises at least one tunable plasmon resonator 502 according to one of the embodiments described herein. For commercial applications embodiments of sensor devices are made as lab-on-chip arrangements with a large number of individual sensor devices identical to the sensor device 500 shown in FIG. 5.

It is noted that details of the structural implementation of the tunable plasmon resonator 502 are not shown in FIG. 5. The tunable plasmon resonator 502 is represented graphically by a plasmon resonance layer 506 on a carrier substrate 504. The carrier substrate 504 is processed on its backside to have a recess 505 that exposes a back surface 506.1 of the plasmon resonance layer on its backside and underneath a sensor chamber 508.

The sensor chamber 508 forms a limited sensing volume that is to be filled with a dielectric fluid containing particles to be detected and identified by a THz spectroscopic method. Side walls 514 near the bottom of the sensor chamber 508 are for instance made of silicon dioxide.

A bottom of the sensor chamber 508 is formed by an upper surface 506.2 of the plasmon resonance layer 506. Small tip-like structures 516 having a vertical extension of less than 1 micrometer are provided on the upper surface 506.2 of the plasmon resonance layer 506 to help catching particles such as biomolecules 518 to be detected and identified by the sensor device 500. This way, the particles are concentrated in the THz/IR near field "hot spot" area to achieve highest sensitivity also in case of ultra-diluted molecules to probe.

The carrier substrate 504 is provided with contact layers 510 and 512 on its bottom side. The contact layers 510 and 512 are used to apply a tuning control voltage to an integrated tuning device (not shown) and thus the plasmon frequency in the plasmon resonance layer 506.

In operation, an external source 520 of electromagnetic radiation in the THz to mid infrared spectral range provides resonance excitation of plasmon polaritons at a desired plasmon frequency controlled by suitable a tuning applied to tuning device setting the plasmon resonance frequency of the plasmon resonance layer 506. Due to an enhanced field strength of the plasmon polaritons near the upper surface 506.1 of the plasmon resonance layer, the particles 518 are exposed to a particularly high field strength, and an electromagnetic radiation containing a frequency response by particles 518 is detected by a detector 522 and recorded for spectral analysis.

The sensor device 500 forms a platform that can be fabricated with standard CMOS/BiCMOS processes, which reduces the manufacturing cost of such sensor platform considerably. The sub THz to mid infrared region operation of doped semiconductor plasmonic structures corresponds to operating wavelengths in the micrometer range. This matches the dimension of biological materials (molecules and cells) that can be sensed in this frequency range.

Figure 6:
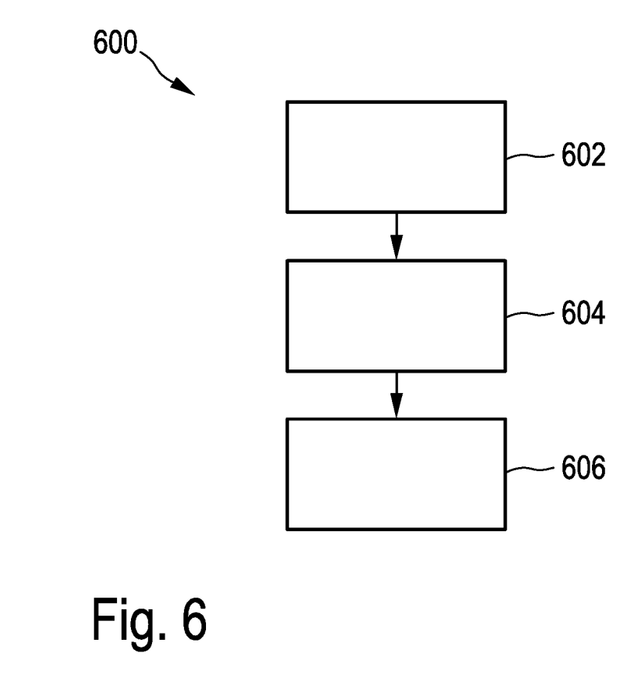
FIG. 6 is a flow diagram of a fabrication process 600 for making a tunable plasmon resonator for operation at frequencies in an infrared frequency range.

FIG. 6 is a flow diagram of a fabrication process 600 for making a tunable plasmon resonator for operation at frequencies in an infrared frequency range.

The method comprises the following steps. In a step 602 a plasmon resonance layer made of a crystalline semiconductor material is fabricated on a carrier substrate. In a step 604, a plasmon resonance region of the plasmon resonance layer is exposed to a sensing volume to be filled with a dielectric fluid. Further, in a step 606 a integrated tuning device is fabricated. It is monolithically integrated into the plasmon resonator. The order of steps 602 to 606 can be modified according to the specifics of a desired fabrication embodiment. Standard CMOS/BiCMOS processes can be used for fabrication, which reduces the manufacturing cost of such a resonator for forming a sensor platform considerably.

What is claimed is:

1. A tunable plasmon resonator, comprising
a plasmon resonance layer made of graphene, a crystalline group-IV-semiconductor material or a crystalline group-III-V semiconductor material, and arranged on a carrier substrate, the plasmon resonance layer having a plasmon resonance region that is exposed to a sensing volume
a tuning device that is integrated into the plasmon resonator and arranged and configured
to modify a density of free charge carriers in the plasmon resonance region of the resonance layer or to modify an effective mass amount of the free charge carriers in the plasmon resonance region of the resonance layer by application of a control voltage to one or more tuning control electrodes of the tuning device, and
to thus set a plasmon frequency of plasmon polaritons in the plasmon resonance region to a desired plasmon frequency value within a plasmon frequency tuning interval, for resonance excitation of plasmon polaritons by incident electromagnetic waves of a frequency corresponding to the set plasmon frequency value.

2. The tunable plasmon resonator according to claim 1, wherein
the plasmon resonance layer is a semiconductor layer of intrinsic conductivity,
the tuning device comprises a first tuning layer formed by a first doped semiconductor layer of a first conductivity type and a second tuning layer formed by a second doped semiconductor layer of a second conductivity type opposite to the first conductivity type, each of the first and second tuning layers being connected with a respective first or second tuning control electrode, and wherein
the plasmon resonance layer is arranged between the first and second tuning layers to form a p-i-n structure, thus allowing an injection of free charge carriers into the plasmon resonance layer in a density amount that depends on an injection control voltage applied via the first and second tuning control electrodes.

3. The tunable plasmon resonator according to claim 1, wherein
the plasmon resonance layer is a semiconductor layer of a first conductivity type,
the tuning device comprises a tuning layer formed by a doped semiconductor layer of a second conductivity type opposite to the first conductivity type, each of the plasmon resonance layer and the tuning layer being connected with a respective first or second tuning control electrode, and wherein
the plasmon resonance layer and the tuning layer are arranged to form a p-n junction, the plasmon resonance region lying a depletion region under application of a maximum reverse bias voltage and containing injected free charge carriers in a density amount that depends on an injection control voltage applied via the first and second tuning control electrodes.

4. The tunable plasmon resonator according to claim 1, wherein
the plasmon resonance layer is a semiconductor layer of a first conductivity type,
the tuning device comprises a tuning layer formed by metal layer each of the plasmon resonance layer and the tuning layer being connected with a respective first or second tuning control electrode, and wherein
the plasmon resonance layer and the tuning layer are arranged to form a Schottky junction, the plasmon resonance region lying a depletion region under application of a maximum reverse bias voltage and containing injected free charge carriers in a density amount that depends on an injection control voltage via the first and second tuning control electrodes.

5. The tunable plasmon resonator according to claim 1, wherein the tuning device comprises a piezoelectric stressor layer configured and arranged to be deformed piezoelectrically and to thus exert stress on a crystal lattice of the plasmon resonance layer with a stress amount depending on a strain control voltage applied to the piezoelectric stressor layer via at least one strain control electrode, thus modifying a lattice strain amount present in the plasmon resonance layer and, in turn, changing an effective mass of the free charge carriers in the plasmon resonance layer.

6. The tunable plasmon resonator according to claim 4, wherein the stressor layer is arranged between the carrier substrate and the plasmon resonance layer.

7. The tunable plasmon resonator according to claim 1, wherein the plasmon resonance layer has different material compositions in different lateral sections, the different material compositions being associated with different effective mass amounts of the free charge carriers in the respective different lateral sections.

8. The tunable plasmon resonator according to claim 1, wherein
the plasmon resonance layer is a semiconductor layer of intrinsic conductivity,
the tuning device comprises a first tuning layer formed by a first doped semiconductor layer of a first conductivity type and a second tuning layer formed by a second doped semiconductor layer of a second conductivity type opposite to the first conductivity type, each of the first and second tuning layers being connected with a respective one of a first and second tuning control electrode,
the plasmon resonance layer is arranged between the first and second tuning layers, thus allowing an injection of free charge carriers into the plasmon resonance layer in a density amount that depends on an injection control voltage applied via the first and second tuning control electrodes, and wherein
the tuning device further comprises a piezoelectric third tuning layer configured and arranged to be deformed piezoelectrically and to thus exert tensile stress on the plasmon resonance layer with a stress amount depending on a strain control voltage applied to the tuning layer via at least one strain control electrode, thus modifying a lattice strain amount present in the plasmon resonance layer and in turn changing an effective mass of the free charge carriers in the plasmon resonance layer.

9. The tunable plasmon resonator according to claim 1, wherein the plasmon resonance layer comprises two layer segments, front faces of the two layer segments facing each other and forming field enhancement regions, wherein the sensing volume is formed by a gap between the front faces.

10. The tunable plasmon resonator according to claim 1, wherein the carrier substrate has an opening that exposes a bottom surface section of the plasmon resonance layer on a second substrate side opposite to a first substrate side comprising the plasmon resonance region.

11. The tunable plasmon resonator according to claim 1, wherein the carrier substrate is made of silicon.

12. A sensor device comprising at least one tunable plasmon resonator according to claim 1, and a sensor chamber enclosing a sensing volume to be filled with a dielectric fluid under test for a detection of particles in the dielectric fluid under test.

13. The sensor device according to claim 12, comprising a plurality of pointed nanostructures extending from a bottom of the sensor chamber into the sensing volume.

14. A sensor arrangement, comprising
  a sensor device according to claim 12
  a tunable emitter arranged and configured to provide electromagnetic radiation in an infrared frequency range incident on the exposed plasmon resonance region of the sensor device; and
  a detector arranged and configured to detect electromagnetic radiation in the infrared frequency range provided by the emitter and either reflected or transmitted by the plasmon resonance region of the sensor device.

15. A method for fabricating a tunable plasmon resonator for operation at frequencies in an infrared frequency range, the method comprising
  fabricating a plasmon resonance layer made of a crystalline semiconductor material on a carrier substrate,
  exposing a plasmon resonance region of the plasmon resonance layer to a sensing volume to be filled with a dielectric fluid;
  fabricating a monolithically integrated tuning device that is arranged and configured
    to modify a density of free charge carriers in the plasmon resonance region of the resonance layer or to modify an effective mass amount of the free charge carriers in the plasmon resonance region of the resonance layer by application of a control voltage to one or more tuning control electrodes of the tuning device, and
    to thus set a plasmon frequency of plasmon polaritons in the plasmon resonance region to a desired plasmon frequency value within a plasmon frequency tuning interval, for resonance excitation of plasmon polaritons by incident electromagnetic waves of a frequency corresponding to the set plasmon frequency value.

* * * * *

UNITED STATES PATENT AND TRADEMARK OFFICE
CERTIFICATE OF CORRECTION

| | |
|---|---|
| PATENT NO. | : 10,054,722 B2 |
| APPLICATION NO. | : 15/460604 |
| DATED | : August 21, 2018 |
| INVENTOR(S) | : Subhajit Guha et al. |

It is certified that error appears in the above-identified patent and that said Letters Patent is hereby corrected as shown below:

On the Title Page

Item (73) insert the name and address of the second Assignee as follows:
--Universität Kassel
Mönchebergstrasse 19
34125 Kassel
Germany--

Signed and Sealed this
Eleventh Day of December, 2018

Andrei Iancu
*Director of the United States Patent and Trademark Office*